US00PP28799P3

(12) United States Plant Patent
Kanazawa

(10) Patent No.: US PP28,799 P3
(45) Date of Patent: Dec. 26, 2017

(54) ***ANEMONE* PLANT NAMED 'APANFARRH'**

(50) Latin Name: *Anemone hupehensis*
Varietal Denomination: APANFARRH

(71) Applicant: Yoshihiro Kanazawa, Fukushima (JP)

(72) Inventor: Yoshihiro Kanazawa, Fukushima (JP)

(73) Assignee: Osco Garden B.V., Aalsmeer (NL)

( * ) Notice: Subject to any disclaimer, the term of this patent is extended or adjusted under 35 U.S.C. 154(b) by 14 days.

(21) Appl. No.: 14/999,405

(22) Filed: May 3, 2016

(65) Prior Publication Data

US 2017/0325373 P1 Nov. 9, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — June Hwu
(74) *Attorney, Agent, or Firm* — C. A. Whealy

(57) ABSTRACT

A new and distinct cultivar of *Anemone* plant named 'APANFARRH', characterized by its upright and compact plant habit; moderately vigorous growth habit; early and freely flowering habit; single-type flowers that are red purple in color and arranged in tight inflorescences; and good garden performance.

2 Drawing Sheets

Botanical designation: *Anemone hupehensis*.
Cultivar denomination: 'APANFARRH'.

BACKGROUND OF THE INVENTION

The present invention relates to a new and distinct cultivar of *Anemone*, botanically known as *Anemone hupehensis* and hereinafter referred to by the name 'APANFARRH'.

The new *Anemone* plant is a product of a planned breeding program conducted by the Inventor in Yamatsuri-machi, Fukushima, Japan. The objective of the breeding program is to create new compact *Anemone* plants with numerous attractive flowers.

The new *Anemone* plant originated from a cross-pollination made by the Inventor on Sep. 14, 2011 in Yamatsuri-machi, Fukushima, Japan of *Anemone hupehensis* 'Diana', not patented, as the female, or seed, parent, with an unnamed selection of *Anemone hupehensis*, not patented, as the male, or pollen, parent. The new *Anemone* plant was discovered and selected by the Inventor as a single flowering plant within the progeny of the stated cross-pollination in a controlled greenhouse environment in Yamatsuri-machi, Fukushima, Japan on Sept. 20, 2013.

Asexual reproduction of the new *Anemone* by root cuttings in a controlled environment in Yamatsuri-machi, Fukushima, Japan since Oct. 10, 2013 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'APANFARRH'. These characteristics in combination distinguish 'APANFARRH' as a new and distinct *Anemone* plant:

1. Upright and compact plant habit.
2. Moderately vigorous growth habit.
3. Early and freely flowering habit.
4. Single-type flowers that are red purple in color and arranged in tight inflorescences.
5. Good garden performance.

Plants of the new *Anemone* can be compared to plants of the female parent, 'Diana'. Plants of the new *Anemone* differ primarily from plants of 'Diana' in the following characteristics:

1. Plants of the new *Anemone* are more compact than plants of 'Diana'.
2. Plants of the new *Anemone* are more freely flowering than plants of 'Diana'.
3. Plants of the new *Anemone* and 'Diana' differ in flower color as plants of 'Diana' have pink-colored flowers.

Plants of the new *Anemone* can be compared to plants of the male parent selection. Plants of the new *Anemone* differ primarily from plants of the male parent selection in the following characteristics:

1. Plants of the new *Anemone* are taller than plants of the male parent selection.
2. Plants of the new *Anemone* are more freely flowering than plants of the male parent selection.
3. Plants of the new *Anemone* and the male parent selection differ in flower color as plants of the male parent selection have pink-colored flowers.

Plants of the new *Anemone* can be compared to plants of *Anemone hupehensis* 'Pretty Lady Susan', disclosed in U.S. Plant Pat. No. 22,331. In side-by-side comparisons, plants of the new *Anemone* and 'Pretty Lady Susan' differ primarily in the following characteristics:

1. Plants of the new *Anemone* are more compact than plants of 'Pretty Lady Susan'.

2. Plants of the new *Anemone* and 'Pretty Lady Susan' differ in flower color as plants of 'Pretty Lady Susan' have deep pink-colored flowers.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'APANFARRH' in a container.

The photograph at the top of the second sheet comprises a close-up view of a typical flowering plant of 'APANFARRH'.

The photograph at the bottom of the second sheet comprises a close-up view of typical leaves of 'APANFARRH'.

DETAILED BOTANICAL DESCRIPTION

The aforementioned photographs and following observations, measurements and values describe plants grown during the summer in 17-cm containers in an outdoor nursery in Mijdrecht, The Netherlands and under cultural practices typical of commercial *Anemone* production. During the production of the plants, day temperatures ranged from 14° C. to 28° C. and night temperatures ranged from 6° C. to 16° C. Plants were four months old when the photographs and description were taken. In the following description, color references are made to The Royal Horticultural Society Colour Chart, 2015 Edition, except where general terms of ordinary dictionary significance are used.

Botanical classification: *Anemone hupehensis* 'APANFARRH'.

Parentage:

*Female, or seed, parent.*—*Anemone hupehensis* 'Diana', not patented.

*Male, or pollen, parent.*—Unnamed selection of *Anemone hupehensis*, not patented.

Propagation:

*Type.*—In vitro propagation.

*Time to initiate roots, summer.*—About 15 days at soil temperatures of 20° C. to 25° C.

*Time to initiate roots, winter.*—About 25 days at soil temperatures of 15° C. to 20° C.

*Root description.*—Medium in thickness, fleshy; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial; upright and compact plant habit with leaves developing from basal rosettes; about 30 basal rosettes developing per plant; narrowly ovate to narrowly oblong in shape; moderately vigorous growth habit.

*Plant height.*—About 37.8 cm.

*Plant diameter.*—About 33.4 cm.

Leaf description:

*Arrangement.*—Alternate; compound with three leaflets per leaf.

*Length, leaves.*—About 9 cm.

*Width, leaves.*—About 8.4 cm.

*Length, leaflets.*—About 6.9 cm.

*Width, leaflets.*—About 3.5 cm.

*Shape, leaves.*—Broadly ovate.

*Shape, leaflets.*—Ovate to broadly ovate.

*Apex, leaflets.*—Acute.

*Base, leaflets.*—Obtuse to hastate.

*Margin, leaflets.*—Serrate.

*Texture and luster, leaflets, upper surface.*—Sparsely pubescent; slightly glossy.

*Texture and luster, leaflets, lower surface.*—Moderately pubescent along veins; dull.

*Venation pattern, leaflets.*—Palmate, laciniate.

*Color.*—Developing leaflets, upper surface: Close to between 143A and 144A. Developing leaflets, lower surface: Close to 143B. Fully expanded leaflets, upper surface: Slightly darker than between NN137A and 147A; venation, close to 144A. Fully expanded leaflets, lower surface: Close to between 148B and 191B; venation, close to 144A.

*Leaf petioles.*—Length: About 11.4 cm. Diameter: About 2 mm. Texture, upper and lower surfaces: Smooth, glabrous. Color, upper and lower surfaces: Close to 144A.

*Leaflet petioles.*—Length: About 1.7 cm. Diameter: About 1 mm. Texture, upper and lower surfaces: Smooth, glabrous. Color, upper and lower surfaces: Close to 143B.

Flower description:

*Flower arrangement and flowering habit.*—Single-type rotate flowers arranged in simple and compound cymes; freely flowering habit with 600 flowers developing per plant; flowers face mostly upright to slightly outwardly.

*Fragrance.*—None detected.

*Natural flowering season.*—Plants of the new *Anemone* begin flowering about 10.5 months after planting and flower during the late summer in The Netherlands.

*Flower longevity.*—Individual flowers last about one week on the plant; flowers not persistent.

*Inflorescence height.*—About 20.3 cm.

*Inflorescence diameter.*—About 12.3 cm.

*Flower diameter.*—About 5.9 cm by 7 cm.

*Flower length (depth).*—About 1.7 cm.

*Flower buds.*—Length: About 1.3 cm. Diameter: About 8 mm. Shape: Ovate. Color: Close to between N186C and 200A; towards the base, close to 145A to 145B.

*Petals.*—Absent.

*Sepals.*—Quantity and arrangement: Five arranged in a single whorl. Length: About 3.4 cm. Width: About 2.4 cm. Shape: Obovate. Apex: Obtuse to broadly acute. Base: Attenuate. Margin: Entire; undulate. Texture and luster, upper surface: Smooth, glabrous; velvety; matte. Texture and luster, lower surface: Densely pubescent; matte. Color: When opening, upper surface: Close to 71A to 71C. When opening, lower surface: Close to 72C to 72D and N186C; towards the base, close to 146D. Fully opened, upper surface: Close to 71A and slightly darker than 71B and 71C; color does not fade with development. Fully opened, lower surface: Close to 71A and NN74C; color does not fade with development.

*Peduncles*.—Length: About 25.3 cm. Diameter: About 3.5 mm. Aspect: Mostly erect to 10° from vertical. Strength: Strong. Texture: Pubescent. Color: Close to 143A.

*Pedicels*.—Length: About 8.4 cm. Diameter: About 0.125 mm. Aspect: Erect to about 30° from the peduncle axis. Strength: Strong. Color: Close to 138A occasionally tinged with close to between N200A to 200B.

*Reproductive organs*.—Androecium: Stamen number per flower: About 190. Filament length: About 6 mm. Filament color: Close to NN155C to NN155D. Anther shape: Reniform. Anther length: About 1 mm. Anther color: Close to 17B. Amount of pollen: Scarce. Pollen color: Close to 11D. Gynoecium: Pistil number per flower: About 200. Pistil length: About 1 mm. Stigma shape: Club-shaped. Stigma color: Close to N144C. Style length: About 0.5 mm. Style color: Close to N144D. Ovary color: Close to 145A.

*Seeds and fruits*.—Seed and fruit development have not been observed on plants of the new *Anemone*.

Garden performance: Plants of the new *Anemone* have been observed to have good garden performance, to tolerate high temperatures of about 35° C. and to be hardy to USDA Hardiness Zone 4.

Pathogen & pest resistance: Plants of the new *Anemone* have not been observed to be resistant to pests and pathogens common to *Anemone* plants.

It is claimed:

1. A new and distinct *Anemone* plant named 'APAN-FARRH' as illustrated and described.

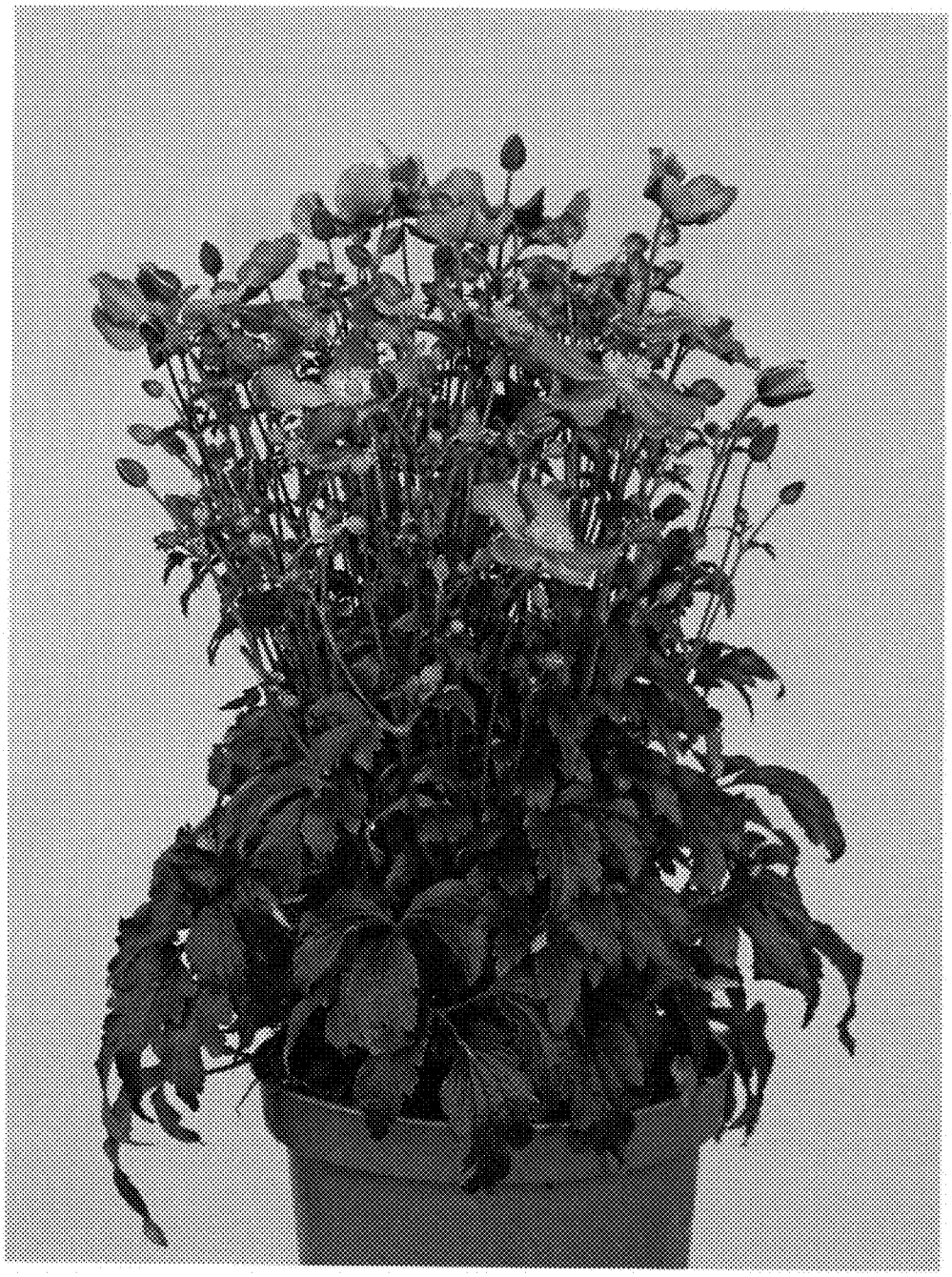

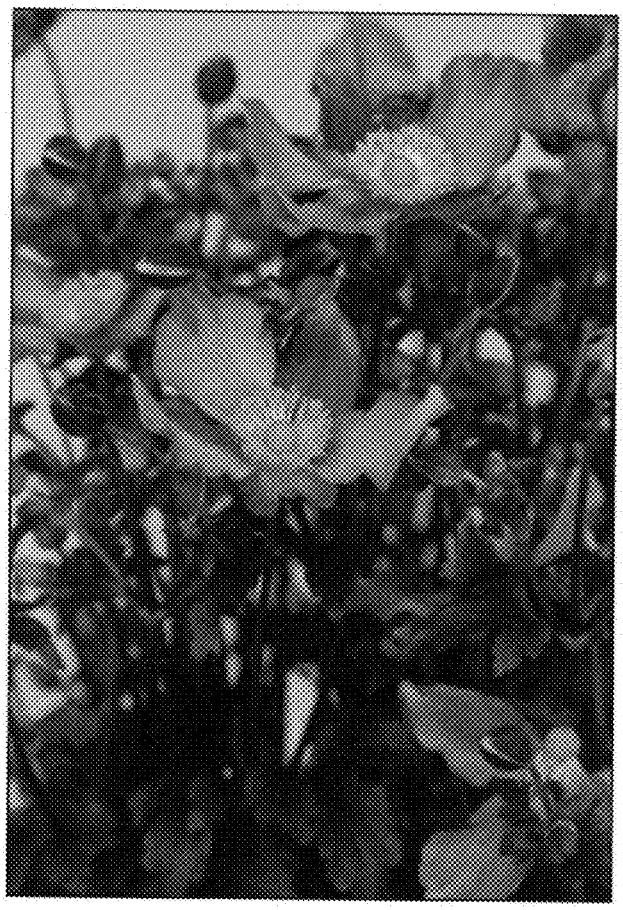
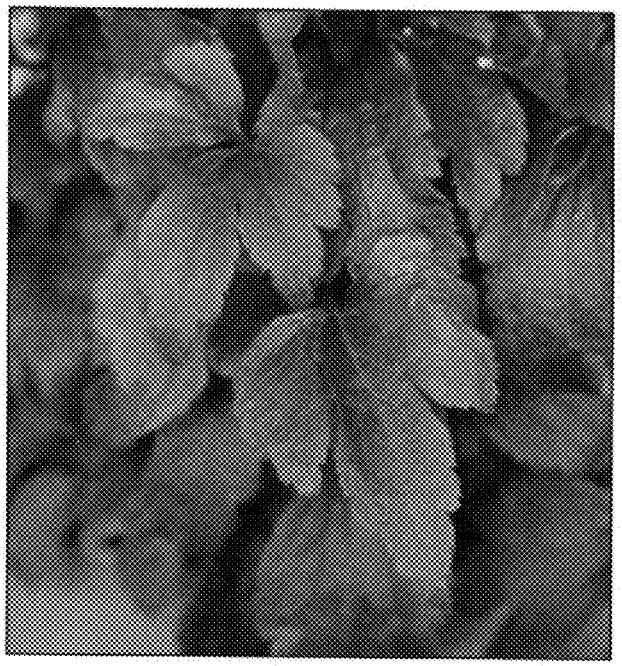

* * * * *